(12) United States Patent
Bathe et al.

(10) Patent No.: US 7,083,942 B2
(45) Date of Patent: Aug. 1, 2006

(54) ALLELES OF THE ACEA GENE FROM CORYNEFORM BACTERIA

(75) Inventors: Brigitte Bathe, Salzkotten (DE); Caroline Kreutzer, Melle (DE); Stephan Hans, Osnabrück (DE)

(73) Assignee: Degussa AG, Düsseldorf (DE)

( * ) Notice: Subject to any disclaimer, the term of this patent is extended or adjusted under 35 U.S.C. 154(b) by 403 days.

(21) Appl. No.: 10/382,986

(22) Filed: Mar. 7, 2003

(65) Prior Publication Data

US 2003/0228678 A1 Dec. 11, 2003

(30) Foreign Application Priority Data

Mar. 9, 2002 (DE) ................................. 102 10 527

(51) Int. Cl.
*C12P 21/04* (2006.01)
*C12P 21/06* (2006.01)

(52) U.S. Cl. ..................... 435/68.1; 435/69.1; 435/71.1

(58) Field of Classification Search ............... 435/69.1, 435/71.1, 68.1
See application file for complete search history.

(56) References Cited

U.S. PATENT DOCUMENTS

| | | |
|---|---|---|
| 4,489,160 A | 12/1984 | Katsumata et al. |
| 5,158,891 A | 10/1992 | Takeda et al. |
| 5,439,822 A | 8/1995 | Katsumata et al. |
| 5,700,661 A | 12/1997 | Katsumata et al. |
| 6,200,785 B1 | 3/2001 | Kreutzer et al. |
| 6,420,151 B1 | 7/2002 | Eikmanns et al. |
| 2002/0065403 A1 | 5/2002 | Eikmanns et al. |
| 2002/0082403 A1 | 6/2002 | Mockel et al. |
| 2002/0106748 A1 | 8/2002 | Mockel et al. |
| 2002/0127663 A1 | 9/2002 | Mockel et al. |
| 2003/0003548 A1 | 1/2003 | Eikmanns et al. |

FOREIGN PATENT DOCUMENTS

| | | |
|---|---|---|
| DE | 195 48 222 | 6/1997 |
| DE | 198 31 609 | 4/1999 |
| DE | 199 47 791 | 4/2001 |
| DE | 199 50 409 | 4/2001 |
| DE | 199 51 975 | 5/2001 |
| DE | 199 59 327 | 6/2001 |
| DE | 199 59 328 | 6/2001 |
| EP | 0 131 171 | 1/1985 |
| EP | 0 197 335 | 10/1986 |
| EP | 0 387 527 | 9/1990 |
| EP | 0 435 132 | 7/1991 |
| EP | 0 699 759 | 3/1996 |
| EP | 1 108 790 | 6/2001 |
| JP | 9-224661 | 9/1997 |
| WO | WO 00/63388 | 10/2000 |
| WO | WO 01/00844 | 1/2001 |
| WO | WO 01/04322 | 1/2001 |
| WO | WO 01/71012 | 9/2001 |

OTHER PUBLICATIONS

Dunican, et al., "High Frequency Transformation of Whole Cells of Amino Acid Producing Coryneform Bacteria Using High Voltage Electroporation," *Bio/Technology* 7:1067-1070 (1989).

Eikmanns, et al., "Identification, Sequence Analysis, and Expression of a *Corynebacterium glutamicum* Gene Cluster Encoding the Three Glycolytic Enzymes Glyceraldehyde-3-Phosphate Dehydrogenase, 3-Phosphoglycerate Kinase, and Triosephosphate Isomerase," *J. Bacteriol.* 174:6076-6086 (1992).

Eikmanns, et al., "A Family of *Coryneformbacterium glutamicum/Escherichia coli* Shuttle Vectors for Cloning, Controlled Gene Expression, and Promoter Probing," *Gene* 102:93-98 (1991).

Molenaar, et al., "Biochemical and Genetic Characterization of the Membrane-Associated Malate Dehydrogenase (Acceptor) from *Coryneformbacterium glutamicum*," *Eur. J. Biochem.* 254:395-403 (1998).

Peoples, et al., "Nucleotide Sequence and Fine Structural Analysis of the *Coryneformbacterium glutamicum* hom-thrB Operon," *Mol. Microbiol.* 2:63-72 (1988).

Schäfer, et al., "High-Frequency Conjugal Plasmid Transfer from Gram-Negative *Escherichia coli* to Various Gram-Positive Coryneform Bacteria," *J. Bacteriol.* 172:1663-1666 (1990).

Schäfer, et al., Increased Fertility of *Coryneformbacterium glutamicum* Recipients in Intergeneric Matings with *Escherichia coli* after Stress Exposure, *Appl. Envir. Microbiol.* 60:756-759 (1994).

Serwold-Davis, et al., "Localization of an Origin of Replication in *Coryneformbacterium Diphtheriae* Broad Host Range Plasmid pNG2 That Also Functions in *Escherichia coli*," *FEMS Microbiol. Lett.* 66:119-124 (1990).

Sonnen, et al., "Characterization os pGA1, a New Plasmid from *Coryneformbacterium glutamicum* LP-6," *Gene* 107:69-74 (1991).

(Continued)

*Primary Examiner*—Mark Navarro
(74) *Attorney, Agent, or Firm*—Michael A. Sanzo; Fitch, Even, Tabin & Flannery

(57) ABSTRACT

The invention relates to alleles of the aceA gene from coryneform bacteria coding for isocitrate lyases and processes for the fermentative production of L-lysine using bacteria that contain these alleles.

10 Claims, 1 Drawing Sheet

OTHER PUBLICATIONS

Tauch, et al., "*Coryneformbacterium glutamicum* DNA is subjected to Methylation-Restriction in *Escherichia coli*," *FEMS Microbiol. Lett. 123*:343-348 (1994).

Thierbach, et al., "Transformation of Spheroplasts and Protoplasts of *Coryneformbacterium glutamicum*," *Appl. Microbiol. Biotechnol. 29*:356-362 (1988).

Von Der Osten, et al., "Molecular Cloning Sequence and Fine-Structural analysis of the *Coryneformbacterium glutamicum fda* Gene: Structural Comparison of *C. glutamicum* Fructose-1,6-Biophosphate Aldolase to Class I and Class II Aldolases," *Mol. Microbiol. 3*:1625-1637 (1989).

Reinscheid, et al., "Characterization of the Isocitrate Lyase Gene from *Corynebacterium glutamicum* and Biochemical Analysis of the Enzyme," *J. Bacteriol. 176*:3474-3483 (1994).

Abstract of Reference AL1 above, retrieved from EMBL Database, Accession No. P42449, XP-002247932.

Abstract of Reference AL1 above, retrieved from EMBL Database, Accession No. X75504, XP-002247933.

Figure 1: Map of plasmid pK18mobsacB_aceA_A332T
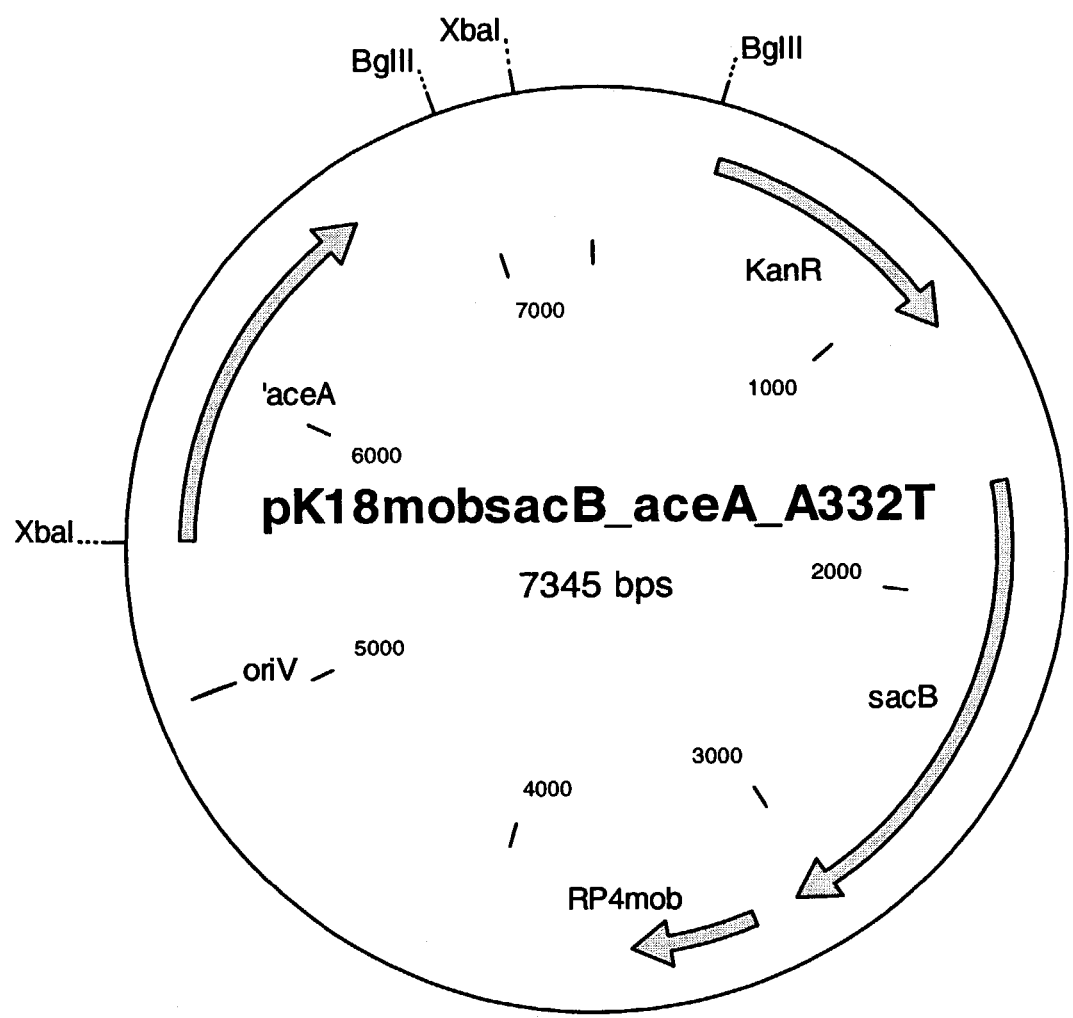

SEQUENCE LISTING

<160> NUMBER OF SEQ ID NOS: 12

<210> SEQ ID NO 1
<211> LENGTH: 1296
<212> TYPE: DNA
<213> ORGANISM: Corynebacterium glutamicum
<220> FEATURE:
<221> NAME/KEY: CDS
<222> LOCATION: (1)..(1296)
<223> OTHER INFORMATION: aceA wild-type gene

<400> SEQUENCE: 1

```
atg tca aac gtt gga aag cca cgt acc gca cag gaa atc cag cag gat      48
Met Ser Asn Val Gly Lys Pro Arg Thr Ala Gln Glu Ile Gln Gln Asp
1               5                  10                  15 tgg gac acc aac cct cgt tgg aac ggc atc acc cgc gac tac acc gca      96
Trp Asp Thr Asn Pro Arg Trp Asn Gly Ile Thr Arg Asp Tyr Thr Ala
            20                  25                  30 gac cag gta gct gat ctg cag ggt tcc gtc atc gag gag cac act ctt     144
Asp Gln Val Ala Asp Leu Gln Gly Ser Val Ile Glu Glu His Thr Leu
        35                  40                  45 gct cgc cgc ggc tca gag atc ctc tgg gac gca gtc acc cag gaa ggt     192
Ala Arg Arg Gly Ser Glu Ile Leu Trp Asp Ala Val Thr Gln Glu Gly
    50                  55                  60 gac gga tac atc aac gcg ctt ggc gca ctc acc ggt aac cag gct gtt     240
Asp Gly Tyr Ile Asn Ala Leu Gly Ala Leu Thr Gly Asn Gln Ala Val
65                  70                  75                  80 cag cag gtt cgt gca ggc ctg aag gct gtc tac ctg tcc ggt tgg cag     288
Gln Gln Val Arg Ala Gly Leu Lys Ala Val Tyr Leu Ser Gly Trp Gln
                85                  90                  95 gtc gca ggt gac gcc aac ctc tcc ggc cac acc tac cct gac cag tcc     336
Val Ala Gly Asp Ala Asn Leu Ser Gly His Thr Tyr Pro Asp Gln Ser
            100                 105                 110 ctc tac cca gcg aac tcc gtt cca agc gtc gtt cgt cgc atc aac aac     384
Leu Tyr Pro Ala Asn Ser Val Pro Ser Val Val Arg Arg Ile Asn Asn
        115                 120                 125 gca ctg ctg cgt tcc gat gaa atc gca cgc acc gaa ggc gac acc tcc     432
Ala Leu Leu Arg Ser Asp Glu Ile Ala Arg Thr Glu Gly Asp Thr Ser
    130                 135                 140 gtt gac aac tgg gtt gtc cca atc gtc gcg gac ggc gaa gct ggc ttc     480
Val Asp Asn Trp Val Val Pro Ile Val Ala Asp Gly Glu Ala Gly Phe
145                 150                 155                 160 ggt gga gca ctc aac gtc tac gaa ctc cag aag gca atg atc gca gct     528
Gly Gly Ala Leu Asn Val Tyr Glu Leu Gln Lys Ala Met Ile Ala Ala
                165                 170                 175
```

```
ggc gct gca ggc acc cac tgg gaa gac cag ctc gct tct gaa aag aag        576
Gly Ala Ala Gly Thr His Trp Glu Asp Gln Leu Ala Ser Glu Lys Lys
        180                 185                 190 tgt ggc cac ctc ggc ggc aag gtt ctg atc cca acc cag cag cac atc        624
Cys Gly His Leu Gly Gly Lys Val Leu Ile Pro Thr Gln Gln His Ile
            195                 200                 205 cgc acc ctg aac tct gcc cgc ctt gca gca gac gtt gca aac acc cca        672
Arg Thr Leu Asn Ser Ala Arg Leu Ala Ala Asp Val Ala Asn Thr Pro
    210                 215                 220 act gtt gtt atc gca cgt acc gac gct gag gca gca acc ctg atc acc        720
Thr Val Val Ile Ala Arg Thr Asp Ala Glu Ala Ala Thr Leu Ile Thr
225                 230                 235                 240 tct gac gtt gat gag cgc gac caa cca ttc atc acc ggt gag cgc acc        768
Ser Asp Val Asp Glu Arg Asp Gln Pro Phe Ile Thr Gly Glu Arg Thr
                245                 250                 255 gca gaa ggc tac tac cac gtc aag aat ggt ctc gag cca tgt atc gca        816
Ala Glu Gly Tyr Tyr His Val Lys Asn Gly Leu Glu Pro Cys Ile Ala
            260                 265                 270 cgt gca aag tcc tac gca cca tac gca gat atg atc tgg atg gag acc        864
Arg Ala Lys Ser Tyr Ala Pro Tyr Ala Asp Met Ile Trp Met Glu Thr
        275                 280                 285 ggc acc cct gac ctg gag ctc gct aag aag ttc gct gaa ggc gtt cgc        912
Gly Thr Pro Asp Leu Glu Leu Ala Lys Lys Phe Ala Glu Gly Val Arg
    290                 295                 300 tct gag ttc cca gac cag ctg ctg tcc tac aac tgc tcc cca tcc ttc        960
Ser Glu Phe Pro Asp Gln Leu Leu Ser Tyr Asn Cys Ser Pro Ser Phe
305                 310                 315                 320 aac tgg tct gca cac ctc gag gca gat gag atc gct aag ttc cag aag       1008
Asn Trp Ser Ala His Leu Glu Ala Asp Glu Ile Ala Lys Phe Gln Lys
                325                 330                 335 gaa ctc ggc gca atg ggc ttc aag ttc cag ttc atc acc ctc gca ggc       1056
Glu Leu Gly Ala Met Gly Phe Lys Phe Gln Phe Ile Thr Leu Ala Gly
            340                 345                 350 ttc cac tcc ctc aac tac ggc atg ttc gac ctg gct tac gga tac gct       1104
Phe His Ser Leu Asn Tyr Gly Met Phe Asp Leu Ala Tyr Gly Tyr Ala
        355                 360                 365 cgc gaa ggc atg acc tcc ttc gtt gac ctg cag aac cgt gag ttc aag       1152
Arg Glu Gly Met Thr Ser Phe Val Asp Leu Gln Asn Arg Glu Phe Lys
    370                 375                 380 gca gct gaa gag cgt ggc ttc acc gct gtt aag cac cag cgt gag gtt       1200
Ala Ala Glu Glu Arg Gly Phe Thr Ala Val Lys His Gln Arg Glu Val
385                 390                 395                 400 ggc gca ggc tac ttc gac cag atc gca acc acc gtt gac ccg aac tct       1248
Gly Ala Gly Tyr Phe Asp Gln Ile Ala Thr Thr Val Asp Pro Asn Ser
                405                 410                 415 tct acc acc gct ttg aag ggt tcc act gaa gaa ggc cag ttc cac aac       1296
Ser Thr Thr Ala Leu Lys Gly Ser Thr Glu Glu Gly Gln Phe His Asn
            420                 425                 430

<210> SEQ ID NO 2
<211> LENGTH: 432
<212> TYPE: PRT
<213> ORGANISM: Corynebacterium glutamicum

<400> SEQUENCE: 2

Met Ser Asn Val Gly Lys Pro Arg Thr Ala Gln Glu Ile Gln Gln Asp
1               5                   10                  15

Trp Asp Thr Asn Pro Arg Trp Asn Gly Ile Thr Arg Asp Tyr Thr Ala
            20                  25                  30
```

```
Asp Gln Val Ala Asp Leu Gln Gly Ser Val Ile Glu Glu His Thr Leu
        35                  40                  45
Ala Arg Arg Gly Ser Glu Ile Leu Trp Asp Ala Val Thr Gln Glu Gly
 50                  55                  60
Asp Gly Tyr Ile Asn Ala Leu Gly Ala Leu Thr Gly Asn Gln Ala Val
 65                  70                  75                  80
Gln Gln Val Arg Ala Gly Leu Lys Ala Val Tyr Leu Ser Gly Trp Gln
                 85                  90                  95
Val Ala Gly Asp Ala Asn Leu Ser Gly His Thr Tyr Pro Asp Gln Ser
                100                 105                 110
Leu Tyr Pro Ala Asn Ser Val Pro Ser Val Val Arg Ile Asn Asn
            115                 120                 125
Ala Leu Leu Arg Ser Asp Glu Ile Ala Arg Thr Glu Gly Asp Thr Ser
    130                 135                 140
Val Asp Asn Trp Val Pro Ile Val Ala Asp Gly Glu Ala Gly Phe
145                 150                 155                 160
Gly Gly Ala Leu Asn Val Tyr Glu Leu Gln Lys Ala Met Ile Ala Ala
                165                 170                 175
Gly Ala Ala Gly Thr His Trp Glu Asp Gln Leu Ala Ser Glu Lys Lys
            180                 185                 190
Cys Gly His Leu Gly Gly Lys Val Leu Ile Pro Thr Gln Gln His Ile
            195                 200                 205
Arg Thr Leu Asn Ser Ala Arg Leu Ala Ala Asp Val Ala Asn Thr Pro
    210                 215                 220
Thr Val Val Ile Ala Arg Thr Asp Ala Glu Ala Thr Leu Ile Thr
225                 230                 235                 240
Ser Asp Val Asp Glu Arg Asp Gln Pro Phe Ile Thr Gly Glu Arg Thr
                245                 250                 255
Ala Glu Gly Tyr Tyr His Val Lys Asn Gly Leu Glu Pro Cys Ile Ala
            260                 265                 270
Arg Ala Lys Ser Tyr Ala Pro Tyr Ala Asp Met Ile Trp Met Glu Thr
    275                 280                 285
Gly Thr Pro Asp Leu Glu Leu Ala Lys Lys Phe Ala Glu Gly Val Arg
    290                 295                 300
Ser Glu Phe Pro Asp Gln Leu Leu Ser Tyr Asn Cys Ser Pro Ser Phe
305                 310                 315                 320
Asn Trp Ser Ala His Leu Glu Ala Asp Glu Ile Ala Lys Phe Gln Lys
                325                 330                 335
Glu Leu Gly Ala Met Gly Phe Lys Phe Gln Phe Ile Thr Leu Ala Gly
            340                 345                 350
Phe His Ser Leu Asn Tyr Gly Met Phe Asp Leu Ala Tyr Gly Tyr Ala
            355                 360                 365
Arg Glu Gly Met Thr Ser Phe Val Asp Leu Gln Asn Arg Glu Phe Lys
    370                 375                 380
Ala Ala Glu Glu Arg Gly Phe Thr Ala Val Lys His Gln Arg Glu Val
385                 390                 395                 400
Gly Ala Gly Tyr Phe Asp Gln Ile Ala Thr Thr Val Asp Pro Asn Ser
                405                 410                 415
Ser Thr Thr Ala Leu Lys Gly Ser Thr Glu Glu Gly Gln Phe His Asn
            420                 425                 430

<210> SEQ ID NO 3
<211> LENGTH: 1296
<212> TYPE: DNA
```

<213> ORGANISM: Corynebacterium glutamicum
<220> FEATURE:
<221> NAME/KEY: CDS
<222> LOCATION: (1)..(1296)
<223> OTHER INFORMATION: aceA-allele
<220> FEATURE:
<221> NAME/KEY: mutation
<222> LOCATION: (994)..(994)
<223> OTHER INFORMATION: G-A Transition

<400> SEQUENCE: 3

| | | | | | | | | | | | | | | | | |
|---|---|---|---|---|---|---|---|---|---|---|---|---|---|---|---|---|
| atg | tca | aac | gtt | gga | aag | cca | cgt | acc | gca | cag | gaa | atc | cag | cag | gat | 48 |
| Met | Ser | Asn | Val | Gly | Lys | Pro | Arg | Thr | Ala | Gln | Glu | Ile | Gln | Gln | Asp | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tgg | gac | acc | aac | cct | cgt | tgg | aac | ggc | atc | acc | cgc | gac | tac | acc | gca | 96 |
| Trp | Asp | Thr | Asn | Pro | Arg | Trp | Asn | Gly | Ile | Thr | Arg | Asp | Tyr | Thr | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| gac | cag | gta | gct | gat | ctg | cag | ggt | tcc | gtc | atc | gag | gag | cac | act | ctt | 144 |
| Asp | Gln | Val | Ala | Asp | Leu | Gln | Gly | Ser | Val | Ile | Glu | Glu | His | Thr | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| gct | cgc | cgc | ggc | tca | gag | atc | ctc | tgg | gac | gca | gtc | acc | cag | gaa | ggt | 192 |
| Ala | Arg | Arg | Gly | Ser | Glu | Ile | Leu | Trp | Asp | Ala | Val | Thr | Gln | Glu | Gly | |
| 50 | | | | | 55 | | | | | 60 | | | | | | |

| | | | | | | | | | | | | | | | | |
|---|---|---|---|---|---|---|---|---|---|---|---|---|---|---|---|---|
| gac | gga | tac | atc | aac | gcg | ctt | ggc | gca | ctc | acc | ggt | aac | cag | gct | gtt | 240 |
| Asp | Gly | Tyr | Ile | Asn | Ala | Leu | Gly | Ala | Leu | Thr | Gly | Asn | Gln | Ala | Val | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| cag | cag | gtt | cgt | gca | ggc | ctg | aag | gct | gtc | tac | ctg | tcc | ggt | tgg | cag | 288 |
| Gln | Gln | Val | Arg | Ala | Gly | Leu | Lys | Ala | Val | Tyr | Leu | Ser | Gly | Trp | Gln | |
| | | | | 85 | | | | | 90 | | | | | 95 | | |

| | | | | | | | | | | | | | | | | |
|---|---|---|---|---|---|---|---|---|---|---|---|---|---|---|---|---|
| gtc | gca | ggt | gac | gcc | aac | ctc | tcc | ggc | cac | acc | tac | cct | gac | cag | tcc | 336 |
| Val | Ala | Gly | Asp | Ala | Asn | Leu | Ser | Gly | His | Thr | Tyr | Pro | Asp | Gln | Ser | |
| | | | 100 | | | | | 105 | | | | | 110 | | | |

| | | | | | | | | | | | | | | | | |
|---|---|---|---|---|---|---|---|---|---|---|---|---|---|---|---|---|
| ctc | tac | cca | gcg | aac | tcc | gtt | cca | agc | gtc | gtt | cgt | cgc | atc | aac | aac | 384 |
| Leu | Tyr | Pro | Ala | Asn | Ser | Val | Pro | Ser | Val | Val | Arg | Arg | Ile | Asn | Asn | |
| | | 115 | | | | | 120 | | | | | 125 | | | | |

| | | | | | | | | | | | | | | | | |
|---|---|---|---|---|---|---|---|---|---|---|---|---|---|---|---|---|
| gca | ctg | ctg | cgt | tcc | gat | gaa | atc | gca | cgc | acc | gaa | ggc | gac | acc | tcc | 432 |
| Ala | Leu | Leu | Arg | Ser | Asp | Glu | Ile | Ala | Arg | Thr | Glu | Gly | Asp | Thr | Ser | |
| 130 | | | | | 135 | | | | | 140 | | | | | | |

| | | | | | | | | | | | | | | | | |
|---|---|---|---|---|---|---|---|---|---|---|---|---|---|---|---|---|
| gtt | gac | aac | tgg | gtt | gtc | cca | atc | gtc | gcg | gac | ggc | gaa | gct | ggc | ttc | 480 |
| Val | Asp | Asn | Trp | Val | Val | Pro | Ile | Val | Ala | Asp | Gly | Glu | Ala | Gly | Phe | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ggt | gga | gca | ctc | aac | gtc | tac | gaa | ctc | cag | aag | gca | atg | atc | gca | gct | 528 |
| Gly | Gly | Ala | Leu | Asn | Val | Tyr | Glu | Leu | Gln | Lys | Ala | Met | Ile | Ala | Ala | |
| | | | | 165 | | | | | 170 | | | | | 175 | | |

| | | | | | | | | | | | | | | | | |
|---|---|---|---|---|---|---|---|---|---|---|---|---|---|---|---|---|
| ggc | gct | gca | ggc | acc | cac | tgg | gaa | gac | cag | ctc | gct | tct | gaa | aag | aag | 576 |
| Gly | Ala | Ala | Gly | Thr | His | Trp | Glu | Asp | Gln | Leu | Ala | Ser | Glu | Lys | Lys | |
| | | | 180 | | | | | 185 | | | | | 190 | | | |

| | | | | | | | | | | | | | | | | |
|---|---|---|---|---|---|---|---|---|---|---|---|---|---|---|---|---|
| tgt | ggc | cac | ctc | ggc | ggc | aag | gtt | ctg | atc | cca | acc | cag | cag | cac | atc | 624 |
| Cys | Gly | His | Leu | Gly | Gly | Lys | Val | Leu | Ile | Pro | Thr | Gln | Gln | His | Ile | |
| | | 195 | | | | | 200 | | | | | 205 | | | | |

| | | | | | | | | | | | | | | | | |
|---|---|---|---|---|---|---|---|---|---|---|---|---|---|---|---|---|
| cgc | acc | ctg | aac | tct | gcc | cgc | ctt | gca | gca | gac | gtt | gca | aac | acc | cca | 672 |
| Arg | Thr | Leu | Asn | Ser | Ala | Arg | Leu | Ala | Ala | Asp | Val | Ala | Asn | Thr | Pro | |
| 210 | | | | | 215 | | | | | 220 | | | | | | |

| | | | | | | | | | | | | | | | | |
|---|---|---|---|---|---|---|---|---|---|---|---|---|---|---|---|---|
| act | gtt | gtt | atc | gca | cgt | acc | gac | gct | gag | gca | gca | acc | ctg | atc | acc | 720 |
| Thr | Val | Val | Ile | Ala | Arg | Thr | Asp | Ala | Glu | Ala | Ala | Thr | Leu | Ile | Thr | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| tct | gac | gtt | gat | gag | cgc | gac | caa | cca | ttc | atc | acc | ggt | gag | cgc | acc | 768 |
| Ser | Asp | Val | Asp | Glu | Arg | Asp | Gln | Pro | Phe | Ile | Thr | Gly | Glu | Arg | Thr | |
| | | | | 245 | | | | | 250 | | | | | 255 | | |

| | | | | | | | | | | | | | | | | |
|---|---|---|---|---|---|---|---|---|---|---|---|---|---|---|---|---|
| gca | gaa | ggc | tac | tac | cac | gtc | aag | aat | ggt | ctc | gag | cca | tgt | atc | gca | 816 |
| Ala | Glu | Gly | Tyr | Tyr | His | Val | Lys | Asn | Gly | Leu | Glu | Pro | Cys | Ile | Ala | |
| | | | 260 | | | | | 265 | | | | | 270 | | | |

```
cgt gca aag tcc tac gca cca tac gca gat atg atc tgg atg gag acc    864
Arg Ala Lys Ser Tyr Ala Pro Tyr Ala Asp Met Ile Trp Met Glu Thr
        275                 280                 285 ggc acc cct gac ctg gag ctc gct aag aag ttc gct gaa ggc gtt cgc    912
Gly Thr Pro Asp Leu Glu Leu Ala Lys Lys Phe Ala Glu Gly Val Arg
    290                 295                 300 tct gag ttc cca gac cag ctg ctg tcc tac aac tgc tcc cca tcc ttc    960
Ser Glu Phe Pro Asp Gln Leu Leu Ser Tyr Asn Cys Ser Pro Ser Phe
305                 310                 315                 320 aac tgg tct gca cac ctc gag gca gat gag atc act aag ttc cag aag   1008
Asn Trp Ser Ala His Leu Glu Ala Asp Glu Ile Thr Lys Phe Gln Lys
                325                 330                 335 gaa ctc ggc gca atg ggc ttc aag ttc cag ttc atc acc ctc gca ggc   1056
Glu Leu Gly Ala Met Gly Phe Lys Phe Gln Phe Ile Thr Leu Ala Gly
            340                 345                 350 ttc cac tcc ctc aac tac ggc atg ttc gac ctg gct tac gga tac gct   1104
Phe His Ser Leu Asn Tyr Gly Met Phe Asp Leu Ala Tyr Gly Tyr Ala
        355                 360                 365 cgc gaa ggc atg acc tcc ttc gtt gac ctg cag aac cgt gag ttc aag   1152
Arg Glu Gly Met Thr Ser Phe Val Asp Leu Gln Asn Arg Glu Phe Lys
    370                 375                 380 gca gct gaa gag cgt ggc ttc acc gct gtt aag cac cag cgt gag gtt   1200
Ala Ala Glu Glu Arg Gly Phe Thr Ala Val Lys His Gln Arg Glu Val
385                 390                 395                 400 ggc gca ggc tac ttc gac cag atc gca acc acc gtt gac ccg aac tct   1248
Gly Ala Gly Tyr Phe Asp Gln Ile Ala Thr Thr Val Asp Pro Asn Ser
                405                 410                 415 tct acc acc gct ttg aag ggt tcc act gaa gaa ggc cag ttc cac aac   1296
Ser Thr Thr Ala Leu Lys Gly Ser Thr Glu Glu Gly Gln Phe His Asn
            420                 425                 430

<210> SEQ ID NO 4
<211> LENGTH: 432
<212> TYPE: PRT
<213> ORGANISM: Corynebacterium glutamicum

<400> SEQUENCE: 4

Met Ser Asn Val Gly Lys Pro Arg Thr Ala Gln Glu Ile Gln Gln Asp
1               5                   10                  15

Trp Asp Thr Asn Pro Arg Trp Asn Gly Ile Thr Arg Asp Tyr Thr Ala
            20                  25                  30

Asp Gln Val Ala Asp Leu Gln Gly Ser Val Ile Glu Glu His Thr Leu
        35                  40                  45

Ala Arg Arg Gly Ser Glu Ile Leu Trp Asp Ala Val Thr Gln Glu Gly
    50                  55                  60

Asp Gly Tyr Ile Asn Ala Leu Gly Ala Leu Thr Gly Asn Gln Ala Val
65                  70                  75                  80

Gln Gln Val Arg Ala Gly Leu Lys Ala Val Tyr Leu Ser Gly Trp Gln
                85                  90                  95

Val Ala Gly Asp Ala Asn Leu Ser Gly His Thr Tyr Pro Asp Gln Ser
            100                 105                 110

Leu Tyr Pro Ala Asn Ser Val Pro Ser Val Val Arg Arg Ile Asn Asn
        115                 120                 125

Ala Leu Leu Arg Ser Asp Glu Ile Ala Arg Thr Glu Gly Asp Thr Ser
    130                 135                 140

Val Asp Asn Trp Val Val Pro Ile Val Ala Asp Gly Glu Ala Gly Phe
145                 150                 155                 160
```

-continued

```
Gly Gly Ala Leu Asn Val Tyr Glu Leu Gln Lys Ala Met Ile Ala Ala
            165                 170                 175

Gly Ala Ala Gly Thr His Trp Glu Asp Gln Leu Ala Ser Glu Lys Lys
        180                 185                 190

Cys Gly His Leu Gly Gly Lys Val Leu Ile Pro Thr Gln Gln His Ile
    195                 200                 205

Arg Thr Leu Asn Ser Ala Arg Leu Ala Ala Asp Val Ala Asn Thr Pro
210                 215                 220

Thr Val Val Ile Ala Arg Thr Asp Ala Glu Ala Thr Leu Ile Thr
225                 230                 235                 240

Ser Asp Val Asp Glu Arg Asp Gln Pro Phe Ile Thr Gly Glu Arg Thr
                245                 250                 255

Ala Glu Gly Tyr Tyr His Val Lys Asn Gly Leu Glu Pro Cys Ile Ala
            260                 265                 270

Arg Ala Lys Ser Tyr Ala Pro Tyr Ala Asp Met Ile Trp Met Glu Thr
        275                 280                 285

Gly Thr Pro Asp Leu Glu Leu Ala Lys Lys Phe Ala Glu Gly Val Arg
    290                 295                 300

Ser Glu Phe Pro Asp Gln Leu Leu Ser Tyr Asn Cys Ser Pro Ser Phe
305                 310                 315                 320

Asn Trp Ser Ala His Leu Glu Ala Asp Glu Ile Thr Lys Phe Gln Lys
                325                 330                 335

Glu Leu Gly Ala Met Gly Phe Lys Phe Gln Phe Ile Thr Leu Ala Gly
            340                 345                 350

Phe His Ser Leu Asn Tyr Gly Met Phe Asp Leu Ala Tyr Gly Tyr Ala
        355                 360                 365

Arg Glu Gly Met Thr Ser Phe Val Asp Leu Gln Asn Arg Glu Phe Lys
    370                 375                 380

Ala Ala Glu Glu Arg Gly Phe Thr Ala Val Lys His Gln Arg Glu Val
385                 390                 395                 400

Gly Ala Gly Tyr Phe Asp Gln Ile Ala Thr Thr Val Asp Pro Asn Ser
                405                 410                 415

Ser Thr Thr Ala Leu Lys Gly Ser Thr Glu Glu Gly Gln Phe His Asn
            420                 425                 430

<210> SEQ ID NO 5
<211> LENGTH: 1605
<212> TYPE: DNA
<213> ORGANISM: Corynebacterium glutamicum
<220> FEATURE:
<221> NAME/KEY: CDS
<222> LOCATION: (258)..(1553)
<223> OTHER INFORMATION: aceA-allele
<220> FEATURE:
<221> NAME/KEY: mutation
<222> LOCATION: (1251)..(1251)
<223> OTHER INFORMATION: G-A Transition

<400> SEQUENCE: 5
tacatccgta ctagcaactc ccccgcccac ttttctgcg aagccagaac tttgcaaact     60
tcacaacagg ggtgaccacc cccgcacaaa acttaaaaac ccaaaccgat tgacgcacca    120
atgcccgatg gagcaatgtg tgaaccacgc caccacgcaa accgatgcac atcacgtcga    180
aacagtgaca gtgcattagc tcatactttg tggtcggcac cgcccattgc gaatcagcac    240
ttaaggaagt gactttg atg tca aac gtt gga aag cca cgt acc gca cag      290
                    Met Ser Asn Val Gly Lys Pro Arg Thr Ala Gln
                     1               5                  10
```

```
                                        -continued gaa atc cag cag gat tgg gac acc aac cct cgt tgg aac ggc atc acc      338
Glu Ile Gln Gln Asp Trp Asp Thr Asn Pro Arg Trp Asn Gly Ile Thr
         15                  20                  25 cgc gac tac acc gca gac cag gta gct gat ctg cag ggt tcc gtc atc      386
Arg Asp Tyr Thr Ala Asp Gln Val Ala Asp Leu Gln Gly Ser Val Ile
     30                  35                  40 gag gag cac act ctt gct cgc cgc ggc tca gag atc ctc tgg gac gca      434
Glu Glu His Thr Leu Ala Arg Arg Gly Ser Glu Ile Leu Trp Asp Ala
 45                  50                  55 gtc acc cag gaa ggt gac gga tac atc aac gcg ctt ggc gca ctc acc      482
Val Thr Gln Glu Gly Asp Gly Tyr Ile Asn Ala Leu Gly Ala Leu Thr
 60                  65                  70                  75 ggt aac cag gct gtt cag cag gtt cgt gca ggc ctg aag gct gtc tac      530
Gly Asn Gln Ala Val Gln Gln Val Arg Ala Gly Leu Lys Ala Val Tyr
                 80                  85                  90 ctg tcc ggt tgg cag gtc gca ggt gac gcc aac ctc tcc ggc cac acc      578
Leu Ser Gly Trp Gln Val Ala Gly Asp Ala Asn Leu Ser Gly His Thr
             95                 100                 105 tac cct gac cag tcc ctc tac cca gcg aac tcc gtt cca agc gtc gtt      626
Tyr Pro Asp Gln Ser Leu Tyr Pro Ala Asn Ser Val Pro Ser Val Val
        110                 115                 120 cgt cgc atc aac aac gca ctg ctg cgt tcc gat gaa atc gca cgc acc      674
Arg Arg Ile Asn Asn Ala Leu Leu Arg Ser Asp Glu Ile Ala Arg Thr
    125                 130                 135 gaa ggc gac acc tcc gtt gac aac tgg gtt gtc cca atc gtc gcg gac      722
Glu Gly Asp Thr Ser Val Asp Asn Trp Val Val Pro Ile Val Ala Asp
140                 145                 150                 155 ggc gaa gct ggc ttc ggt gga gca ctc aac gtc tac gaa ctc cag aag      770
Gly Glu Ala Gly Phe Gly Gly Ala Leu Asn Val Tyr Glu Leu Gln Lys
                160                 165                 170 gca atg atc gca gct ggc gct gca ggc acc cac tgg gaa gac cag ctc      818
Ala Met Ile Ala Ala Gly Ala Ala Gly Thr His Trp Glu Asp Gln Leu
            175                 180                 185 gct tct gaa aag aag tgt ggc cac ctc ggc ggc aag gtt ctg atc cca      866
Ala Ser Glu Lys Lys Cys Gly His Leu Gly Gly Lys Val Leu Ile Pro
        190                 195                 200 acc cag cag cac atc cgc acc ctg aac tct gcc cgc ctt gca gca gac      914
Thr Gln Gln His Ile Arg Thr Leu Asn Ser Ala Arg Leu Ala Ala Asp
    205                 210                 215 gtt gca aac acc cca act gtt gtt atc gca cgt acc gac gct gag gca      962
Val Ala Asn Thr Pro Thr Val Val Ile Ala Arg Thr Asp Ala Glu Ala
220                 225                 230                 235 gca acc ctg atc acc tct gac gtt gat gag cgc gac caa cca ttc atc      1010
Ala Thr Leu Ile Thr Ser Asp Val Asp Glu Arg Asp Gln Pro Phe Ile
                240                 245                 250 acc ggt gag cgc acc gca gaa ggc tac tac cac gtc aag aat ggt ctc      1058
Thr Gly Glu Arg Thr Ala Glu Gly Tyr Tyr His Val Lys Asn Gly Leu
            255                 260                 265 gag cca tgt atc gca cgt gca aag tcc tac gca cca tac gca gat atg      1106
Glu Pro Cys Ile Ala Arg Ala Lys Ser Tyr Ala Pro Tyr Ala Asp Met
        270                 275                 280 atc tgg atg gag acc ggc acc cct gac ctg gag ctc gct aag aag ttc      1154
Ile Trp Met Glu Thr Gly Thr Pro Asp Leu Glu Leu Ala Lys Lys Phe
    285                 290                 295 gct gaa ggc gtt cgc tct gag ttc cca gac cag ctg ctg tcc tac aac      1202
Ala Glu Gly Val Arg Ser Glu Phe Pro Asp Gln Leu Leu Ser Tyr Asn
300                 305                 310                 315 tgc tcc cca tcc ttc aac tgg tct gca cac ctc gag gca gat gag atc      1250
Cys Ser Pro Ser Phe Asn Trp Ser Ala His Leu Glu Ala Asp Glu Ile
                320                 325                 330
```

-continued

```
act aag ttc cag aag gaa ctc ggc gca atg ggc ttc aag ttc cag ttc      1298
Thr Lys Phe Gln Lys Glu Leu Gly Ala Met Gly Phe Lys Phe Gln Phe
         335                 340                 345 atc acc ctc gca ggc ttc cac tcc ctc aac tac ggc atg ttc gac ctg      1346
Ile Thr Leu Ala Gly Phe His Ser Leu Asn Tyr Gly Met Phe Asp Leu
     350                 355                 360 gct tac gga tac gct cgc gaa ggc atg acc tcc ttc gtt gac ctg cag      1394
Ala Tyr Gly Tyr Ala Arg Glu Gly Met Thr Ser Phe Val Asp Leu Gln
 365                 370                 375 aac cgt gag ttc aag gca gct gaa gag cgt ggc ttc acc gct gtt aag      1442
Asn Arg Glu Phe Lys Ala Ala Glu Glu Arg Gly Phe Thr Ala Val Lys
380                 385                 390                 395 cac cag cgt gag gtt ggc gca ggc tac ttc gac cag atc gca acc acc      1490
His Gln Arg Glu Val Gly Ala Gly Tyr Phe Asp Gln Ile Ala Thr Thr
                 400                 405                 410 gtt gac ccg aac tct tct acc acc gct ttg aag ggt tcc act gaa gaa      1538
Val Asp Pro Asn Ser Ser Thr Thr Ala Leu Lys Gly Ser Thr Glu Glu
             415                 420                 425 ggc cag ttc cac aac taggacctac aggttctgac aatttaaatc tccctacatc     1593
Gly Gln Phe His Asn
         430 tgtacaacgg at                                                        1605

<210> SEQ ID NO 6
<211> LENGTH: 432
<212> TYPE: PRT
<213> ORGANISM: Corynebacterium glutamicum

<400> SEQUENCE: 6

Met Ser Asn Val Gly Lys Pro Arg Thr Ala Gln Glu Ile Gln Gln Asp
1               5                   10                  15

Trp Asp Thr Asn Pro Arg Trp Asn Gly Ile Thr Arg Asp Tyr Thr Ala
             20                  25                  30

Asp Gln Val Ala Asp Leu Gln Gly Ser Val Ile Glu Glu His Thr Leu
         35                  40                  45

Ala Arg Arg Gly Ser Glu Ile Leu Trp Asp Ala Val Thr Gln Glu Gly
     50                  55                  60

Asp Gly Tyr Ile Asn Ala Leu Gly Ala Leu Thr Gly Asn Gln Ala Val
65                  70                  75                  80

Gln Gln Val Arg Ala Gly Leu Lys Ala Val Tyr Leu Ser Gly Trp Gln
                 85                  90                  95

Val Ala Gly Asp Ala Asn Leu Ser Gly His Thr Tyr Pro Asp Gln Ser
            100                 105                 110

Leu Tyr Pro Ala Asn Ser Val Pro Ser Val Val Arg Arg Ile Asn Asn
        115                 120                 125

Ala Leu Leu Arg Ser Asp Glu Ile Ala Arg Thr Glu Gly Asp Thr Ser
    130                 135                 140

Val Asp Asn Trp Val Val Pro Ile Val Ala Asp Gly Glu Ala Gly Phe
145                 150                 155                 160

Gly Gly Ala Leu Asn Val Tyr Glu Leu Gln Lys Ala Met Ile Ala Ala
                165                 170                 175

Gly Ala Ala Gly Thr His Trp Glu Asp Gln Leu Ala Ser Glu Lys Lys
            180                 185                 190

Cys Gly His Leu Gly Gly Lys Val Leu Ile Pro Thr Gln Gln His Ile
        195                 200                 205
```

```
Arg Thr Leu Asn Ser Ala Arg Leu Ala Ala Asp Val Ala Asn Thr Pro
    210                 215                 220

Thr Val Ile Ala Arg Thr Asp Ala Glu Ala Ala Thr Leu Ile Thr
225                 230                 235                 240

Ser Asp Val Asp Glu Arg Asp Gln Pro Phe Ile Thr Gly Glu Arg Thr
                245                 250                 255

Ala Glu Gly Tyr Tyr His Val Lys Asn Gly Leu Glu Pro Cys Ile Ala
            260                 265                 270

Arg Ala Lys Ser Tyr Ala Pro Tyr Ala Asp Met Ile Trp Met Glu Thr
        275                 280                 285

Gly Thr Pro Asp Leu Glu Leu Ala Lys Lys Phe Ala Glu Gly Val Arg
    290                 295                 300

Ser Glu Phe Pro Asp Gln Leu Leu Ser Tyr Asn Cys Ser Pro Ser Phe
305                 310                 315                 320

Asn Trp Ser Ala His Leu Glu Ala Asp Glu Ile Thr Lys Phe Gln Lys
                325                 330                 335

Glu Leu Gly Ala Met Gly Phe Lys Phe Gln Phe Ile Thr Leu Ala Gly
            340                 345                 350

Phe His Ser Leu Asn Tyr Gly Met Phe Asp Leu Ala Tyr Gly Tyr Ala
        355                 360                 365

Arg Glu Gly Met Thr Ser Phe Val Asp Leu Gln Asn Arg Glu Phe Lys
    370                 375                 380

Ala Ala Glu Glu Arg Gly Phe Thr Ala Val Lys His Gln Arg Glu Val
385                 390                 395                 400

Gly Ala Gly Tyr Phe Asp Gln Ile Ala Thr Thr Val Asp Pro Asn Ser
                405                 410                 415

Ser Thr Thr Ala Leu Lys Gly Ser Thr Glu Glu Gly Gln Phe His Asn
            420                 425                 430

<210> SEQ ID NO 7
<211> LENGTH: 1633
<212> TYPE: DNA
<213> ORGANISM: Artificial Sequence
<220> FEATURE:
<223> OTHER INFORMATION: PCR-product containing a 3 -terminal Region of
      the aceA-allele (aceA_A332T) and the downstream region
<220> FEATURE:
<221> NAME/KEY: misc_feature
<222> LOCATION: (1)..(1633)
<223> OTHER INFORMATION: PCR-product
<220> FEATURE:
<221> NAME/KEY: mutation
<222> LOCATION: (791)..(791)
<223> OTHER INFORMATION: G-A Transition

<400> SEQUENCE: 7
gatctagatt ggcgcactca ccggtaacca ggctgttcag caggttcgtg caggcctgaa      60
ggctgtctac ctgtccggtt ggcaggtcgc aggtgacgcc aacctctccg gccacaccta     120
ccctgaccag tccctctacc cagcgaactc cgttccaagc gtcgttcgtc gcatcaacaa     180
cgcactgctg cgttccgatg aaatcgcacg caccgaaggc gacacctccg ttgacaactg     240
ggttgtccca atcgtcgcgg acggcgaagc tggcttcggt ggagcactca acgtctacga     300
actccagaag gcaatgatcg cagctggcgc tgcaggcacc cactgggaag accagctcgc     360
ttctgaaaag aagtgtggcc acctcggcgg caaggttctg atcccaaccc agcagcacat     420 ccgcacccctg aactctgccc gccttgcagc agacgttgca aacaccccaa ctgttgttat     480
cgcacgtacc gacgctgagg cagcaaccct gatcacctct gacgttgatg agcgcgacca     540
```

```
accattcatc accggtgagc gcaccgcaga aggctactac cacgtcaaga atggtctcga      600
gccatgtatc gcacgtgcaa agtcctacgc accatacgca gatatgatct ggatggagac      660
cggcacccct gacctggagc tcgctaagaa gttcgctgaa ggcgttcgct ctgagttccc      720
agaccagctg ctgtcctaca actgctcccc atccttcaac tggtctgcac acctcgaggc      780
agatgagatc actaagttcc agaaggaact cggcgcaatg ggcttcaagt tccagttcat      840
caccctcgca ggcttccact ccctcaacta cggcatgttc gacctggctt acggatacgc      900
tcgcgaaggc atgacctcct tcgttgacct gcagaaccgt gagttcaagg cagctgaaga      960
gcgtggcttc accgctgtta agcaccagcg tgaggttggc gcaggctact cgaccagat     1020 cgcaaccacc gttgacccga actcttctac caccgctttg aagggttcca ctgaagaagg     1080
ccagttccac aactaggacc tacaggttct gacaatttaa atctccctac atctgtacaa     1140
cggatgtagg gagttttcc ttatatatgc cctccacaaa tccctatcg tgtgagatgt      1200 gttcatagg tgcccccaac gttgcctgtt gactgcaaat tttccgaaag aatccataaa      1260
ctacttcttt aagtcgccag attaaagtcg tcaatgaaag gacatacatg tctatttccc      1320
gcaccgtctt cggcatcgca gccaccgcag ccctgtctgc agctctcgtt gcgtgttctc      1380
cacctcacca gcaggattcc ccagtccagc gcaccaatga gatcttgact acttctcaga      1440
acccaacttc tgcgagcagc acctcaacct cttccgcaac gactacttcc tcagctcctg      1500
tggaagagga cgtagagatc gttgtttcac cagcagcgtt ggtggacggt gagcaggtta      1560
ccttcgaaat ctctggactt gatccagagg gcggctacta cgcagcgatc tgcgattccg      1620
tagcgtctag atc                                                        1633
```

<210> SEQ ID NO 8
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer aceA-A1

<400> SEQUENCE: 8
tacatccgta ctagcaactc                                                   20

<210> SEQ ID NO 9
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer aceA-A2

<400> SEQUENCE: 9
atccgttgta cagatgtagg                                                   20

<210> SEQ ID NO 10
<211> LENGTH: 28
<212> TYPE: DNA
<213> ORGANISM: Artificial Sequence
<220> FEATURE:
<223> OTHER INFORMATION: Primer aceA_XL-A1
<220> FEATURE:
<221> NAME/KEY: misc_feature
<222> LOCATION: (1)..(28)
<223> OTHER INFORMATION: Primer aceA_XL-A1

```
-continued

<400> SEQUENCE: 10
gatctagatt ggcgcactca ccggtaac                                              28

<210> SEQ ID NO 11
<211> LENGTH: 28
<212> TYPE: DNA
<213> ORGANISM: Artificial Sequence
<220> FEATURE:
<223> OTHER INFORMATION: Primer aceA_XL-A2
<220> FEATURE:
<221> NAME/KEY: misc_feature
<222> LOCATION: (1)..(28)
<223> OTHER INFORMATION: Primer aceA_XL-A2

<400> SEQUENCE: 11
gatctagacg ctacggaatc gcagatcg                                              28

<210> SEQ ID NO 12
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer GATC-10790

<400> SEQUENCE: 12
accgcagaag gctactacca                                                       20
```

ALLELES OF THE ACEA GENE FROM CORYNEFORM BACTERIA

CROSS REFERENCE TO RELATED APPLICATIONS

The present application claims priority to German application no. 102 10 527.8, filed Mar. 9, 2002, which is incorporated in its entirety herein by reference.

FIELD OF THE INVENTION

The present invention relates to alleles of the aceA gene from coryneform bacteria that code for variants of isocitrate lyase and processes for the production of L-lysine using bacteria that contain these alleles.

PRIOR ART

The amino acid L-lysine is widely used in human medicine and in the pharmaceutical industry, in the foodstuffs industry, and most especially in animal nutrition.

It is known to produce amino acids by fermentation of strains of coryneform bacteria, in particular *Corynebacterium glutamicum*. On account of their great importance efforts are constantly being made to improve the production processes. Process improvements may relate to fermentation technology measures, such as for example stirring and provision of oxygen, or the composition of the nutrient media, such as for example the sugar concentration during the fermentation, or the working-up to the product form, for example by ion exchange chromatography, or the intrinsic performance properties of the microorganism itself.

Methods involving mutagenesis, selection and mutant choice are employed in order to improve the performance properties of these microorganisms. In this way strains are obtained that are resistant to antimetabolites or that are auxotrophic for regulatorily important metabolites, and that produce amino acids. A known antimetabolite is the lysine analogue S-(2-aminoethyl)-L-cysteine (AEC).

For some years methods of recombinant DNA technology have also been used to improve the strain of corynebacterium strains producing L-amino acid by amplifying individual amino acid biosynthesis genes and investigating the effect on the amino acid production.

The nucleotide sequence of the *Corynebacterium glutamicum* gene coding for isocitrate lyase may be found in patent application WO 01/00844 as Sequence No. 591 and as Sequence No. 589, as well as in patent application U.S. Pat. No. 5,439,822 as Sequence No. 3.

Furthermore, the nucleotide sequence of the *Corynebacterium glutamicum* gene coding for isocitrate lyase may be found in patent application EP-A-1108790 as Sequence No. 3489 and as Sequence No. 7067, as well as in patent application U.S. Pat. No. 5,700,661 as Sequence No. 3.

The nucleotide sequence is also deposited in the databank of the National Center for Biotechnology Information (NCBI) of the National Library of Medicine (Bethesda, Md., USA) under the Accession Nos. X75504, AX065465, AX065463, I86191, I13693, AX127151, AX123573 and L28760.

OBJECT OF THE INVENTION

The inventors have been concerned with the object of providing new ways for the improved production of L-lysine.

SUMMARY OF THE INVENTION

Wherever L-lysine or lysine are mentioned hereinafter, this is understood to denote not only the bases but also the salts, such as for example lysine monohydrochloride or lysine sulfate.

The present invention provides nucleotide sequences (DNA) derived from coryneform bacteria, in particular *Corynebacterium glutamicum*, that are capable of replication and code for the enzyme isocitrate lyase, wherein the associated amino acid sequences in SEQ ID No. 2 contain at least at Position 332 each proteinogenic amino acid with the exception of L-alanine.

The invention furthermore provides a nucleotide sequence (DNA) derived from coryneform bacteria, in particular *Corynebacterium glutamicum*, that is capable of replication and codes for the enzyme isocitrate lyase, wherein the associated amino acid sequence contains L-threonine at least at Position 332, shown in SEQ ID No. 4.

The invention also provides a nucleotide sequence (DNA) derived from coryneform bacteria, in particular *Corynebacterium glutamicum*, that is capable of replication and codes for the enzyme isocitrate lyase, whose base sequence contains adenine at Position 994, shown in SEQ ID No. 3.

The invention furthermore provides plasmids (vectors) that contain the nucleotide sequences according to the invention and that optionally replicate in coryneform bacteria.

The invention in addition provides bacteria, in particular coryneform bacteria, that contain the nucleotide sequences according to the invention and in which the nucleotide sequences coding for isocitrate lyase are over-expressed, wherein in the associated amino acid sequences a different proteinogenic amino acid is contained at least at Position 332 of SEQ ID No. 2.

DETAILED DESCRIPTION OF THE INVENTION

The bacteria may be bacteria that contain the nucleotide sequences according to the invention in isolated form. Furthermore the bacteria may be mutants that are produced and isolated using conventional in vivo mutagenesis methods and that contain the nucleotide sequences according to the invention or the mutation accordingly at their natural position in the chromosome. Finally, the bacteria may also be recombinant bacteria.

Over-expression is understood to mean an increase in the intracellular concentration or activity of the isocitrate lyases according to the invention.

By means of the over-expression measures the activity or concentration of the corresponding protein is increased in general by at least 10%, 25%, 50%, 75%, 100%, 150%, 200%, 300%, 400% or 500%, at most up to 1000% or 2000%, referred to the activity or concentration of the protein in the starting microorganism.

In order to achieve an over-expression the number of copies of the corresponding gene can be increased, or the promoter and regulation region or the ribosome binding site, which is located upstream of the structure gene, can be mutated. Expression cassettes that are incorporated upstream of the structure gene act in the same way. By means of inducible promoters it is also possible to increase the expression in the course of the fermentative L-lysine production. The expression is similarly improved by measures aimed at increasing the lifetime of the m-RNA. Furthermore, the enzyme activity is similarly enhanced by preventing the breakdown of the enzyme protein. The genes or gene constructs may either be present in plasmids with different numbers of copies, or may be integrated in the chromosome and amplified. Alternatively, an over-expression of the relevant genes can also be achieved by altering the composition of the media and culture conditions.

In order to increase the number of copies of the aceA-alleles according to the invention, plasmids that are replicated in coryneform bacteria are suitable. Numerous known plasmid vectors such as for example pZ1 (Menkel et al., Applied and Environmental Microbiology (1989) 64: 549–554), pEKEx 1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors such as for example those that are based on pCG4 (U.S. Pat. No. 4,489,160), or pNG2 (Serwold-Davis et al., FEMS Microbiology Letters 66, 119–124 (1990)) or pAG1 (U.S. Pat. No. 5,158,891) may be used in a similar way.

Furthermore, the process of chromosomal gene amplification may be used to increase the number of copies, as has been described for example by Reinscheid et al. (Applied and Environmental Microbiology 60, 126–132 (1994)) for the duplication or amplification of the hom-thrB operon. In this method the complete gene or allele is cloned in a plasmid vector that can replicate in a host (typically $E.$ $coli$) but not in $C.$ $glutamicum$. Suitable vectors are for example pSUP301 (Simon et al., Bio/Technology 1, 784–791 (1983)), pK18mob or pK19mob (Schäfer et al., Gene 145, 69–73 (1994)), pGEM-T (Promega Corporation, Madison, Wis., USA), pCR2.1-TOPO (Shuman, Journal of Biological Chemistry 269:32678–84 (1994); U.S. Pat. No. 5,487,993), pCR® Blunt (Invitrogen, Groningen, Netherlands; Bernard et al., Journal of Molecular Biology, 234: 534–541 (1993)), pEM1 (Schrumpf et al., Journal of Bacteriology 173:4510–4516 (1991)) or pBGS8 (Spratt et al., Gene 41: 337–342 (1986)). The plasmid vector that contains the gene or allele to be amplified is then transferred by conjugation or transformation into the desired strain of $C.$ $glutamicum$. The method of conjugation has been described for example by Schäfer et al. (Applied and Environmental Microbiology 60, 756–759 (1994)). Methods of transformation are described for example by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a crossover event the resulting strain contains at least two copies of the relevant gene or allele.

The present invention provides preferably endogenous nucleotide sequences (DNA) derived from coryneform bacteria that are capable of replication and code for the enzyme isocitrate lyase, wherein in the associated amino acid sequences the L-alanine at Position 332 of SEQ ID No. 2 is replaced by another proteinogenic amino acid, in particular L-threonine, shown in SEQ ID No 4. The present invention also provides preferably endogenous nucleotide sequences (DNA) derived from coryneform bacteria that are capable of replication and code for the enzyme isocitrate lyase, whose associated base sequence contains adenine at Position 994, as shown in SEQ ID No. 3.

The present invention also provides those nucleotide sequences that are substantially identical to the afore-described nucleotide sequences. Such sequences include nucleotide sequences that code for variants of isocitrate lyase and that in addition to the afore-described change at Position 332 of SEQ ID No. 2 contain at least one further, in particular conservative amino acid replacement. Also, such sequences include nucleotide sequences that code for variants of isocitrate lyase and that a change at any Position of SEQ ID No. 2 of at least one conservative amino acid replacement.

With aromatic amino acids conservative replacements are referred to if phenylalanine, tryptophan and tyrosine are replaced by one another. With hydrophobic amino acids conservative replacements are referred to if leucine, isoleucine and valine are replaced with one another. With polar amino acids conservative replacements are referred to if glutamine and asparagine are replaced by one another. With basic amino acids conservative replacements are referred to if arginine, lysine and histidine are replaced by one another. With acidic amino acids conservative replacements are referred to if aspartic acid and glutamic acid are replaced by one another. With amino acid containing hydroxyl groups conservative replacements are referred to if serine and threonine are replaced by one another.

With regard to substantially identical nucleic acids, these also include those nucleotide sequences that code for variants of isocitrate lyase and that in addition to the described change at Position 332 of SEQ ID No. 2, contain at the N-terminus or C-terminus an extension or shortening of at least one (1) amino acid. This extension or shortening involves not more than 50, 40, 30, 20, 10, 5, 3 or 2 amino acids or amino acid radicals.

The present invention likewise provides nucleic acids that are derived from or have their origin in the genus Corynebacterium, in particular of the species $Corynebacterium$ $glutamicum$, and code for an isocitrate lyase, and that contain an amino acid sequence corresponding to Positions 327 to 337, or Positions 322 to 342 or 312 to 352 according to SEQ ID No. 4.

The terms "endogenous genes" or "endogenous nucleotide sequences" are understood to mean the genes or nucleotide sequences or alleles present in the population of a species.

The invention also relates to vectors (plasmids) that contain the aforementioned nucleotide sequences and replicate in coryneform bacteria.

Also claimed are bacteria, in particular coryneform bacteria, in which the aforementioned nucleotide sequence(s) coding for the enzyme isocitrate lyase are present. These are typically over-expressed.

The present invention provides a process for the production of L-lysine or feedstuffs additives containing L-lysine, in which the following steps are carried out:

a) fermentation of coryneform bacteria that contain the endogenous nucleotide sequences coding for the enzyme isocitrate lyase, wherein in the associated amino acid sequences at least the L-alanine at Position 332 is replaced by another proteinogenic amino acid, preferably L-threonine.

The alleles of the endogenous isocitrate lyase gene are possibly over-expressed under conditions that are suitable for the formation of the enzyme isocitrate lyase.

b) Enrichment of the L-lysine in the fermentation broth, c) isolation of the L-lysine or feedstuffs additive containing L-lysine from the fermentation broth, optionally d) with constituents from the fermentation broth and/or from the biomass (>0 to 100%).

Proteinogenic amino acids are understood to mean all amino acids that are constituents of proteins or polypeptides. These include in particular: L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine.

The wild form of the aceA gene is contained in wild type strains of coryneform bacteria, in particular of the genus Corynebacterium. The sequence of the wild type gene of Corynebacterium glutamicum is shown in SEQ ID No. 1. The wild type protein is shown in SEQ ID No. 2.

In connection with the genus Corynebacterium, the species Corynebacterium glutamicum known to specialists in the field should in particular be mentioned. Known wild type strains of the species Corynebacterium glutamicum are for example Corynebacterium glutamicum ATCC13032
Corynebacterium acetoglutamicum ATCC15806
Corynebacterium acetoacidophilum ATCC13870
Corynebacterium melassecola ATCC17965
Corynebacterium thermoaminogenes FERM BP-1539
Brevibacterium flavum ATCC14067
Brevibacterium lactofermentum ATCC13869 and
Brevibacterium divaricatum ATCC14020.

In order to produce the aceA alleles according to the invention that code for variants of isocitrate lyase, characterized by an amino acid replacement at least at Position 332 of SEQ ID No. 2, mutagenesis methods described in the prior art are used. In this way strains can be produced and isolated that contain the afore-described mutation in the aceA gene or the nucleotide sequences according to the invention.

For the mutagenesis conventional in vivo mutagenesis methods with cell populations may be employed, using mutagenic substances such as for example N-methyl-N'-nitro-N-nitrosoguanidine or ultraviolet light.

In addition in vitro methods may be used for the mutagenesis, such as for example a treatment with hydroxylamine (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992) or mutagenic oligonucleotides (T. A. Brown: Gentechnologie für Einsteiger, Spektrum Akademischer Verlag, Heidelberg, 1993) or the polymerase chain reaction (PCR) as described in the handbook by Newton and Graham (PCR, Spektrum Akademischer Verlag, Heidelberg, 1994).

Further details and instructions for producing mutations may be obtained from the prior art and known textbooks on genetics and molecular biology, such as for example the textbook by Knippers ("Molekulare Genetik", 6$^{th}$ Edition, Georg Thieme verlag, Stuttgart, Germany, 1995), that by Winnacker ("Gene und Klone", VCH Verlagsgesellschaft, Weinheim, Germany, 1990) or that by Hagemann ("Allgemeine Genetik", Gustav Fischer verlag, Stuttgart, 1986).

When using in vitro methods the aceA gene described in the prior art is amplified by means of the polymerase chain reaction starting from isolated whole DNA of a wild type strain, possibly cloned in suitable plasmid vectors, and the DNA is then subjected to the mutagenesis process. The person skilled in the art can find details and instructions on the amplification of DNA sequences by means of the polymerase chain reaction (PCR) in, inter alia, the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994). Suitable aceA alleles are then selected and investigated with the afore-described processes.

The present invention accordingly provides a new aceA allele coding for a variant of isocitrate lyase, which is shown in SEQ ID No. 3.

The aceA alleles according to the invention may be transferred into suitable strains by the process of gene replacement, as described by Schwarzer and Pühler (Bio/Technology 9, 84–87 (1991)) or Peters-Wendisch et al. (Microbiology 144, 915–927 (1998)). The corresponding aceA allele is in this connection cloned in a vector that is non-replicative for *C. glutamicum*, such as for example pK18mobsacB or pK19mobsacB (Jäger et al., Journal of Bacteriology 174: 5462–65 (1992)) or pCR® Blunt (Invitrogen, Groningen, Netherlands; Bernard et al., Journal of Molecular Biology, 234: 534–541 (1993)) and this is then transferred by transformation or conjugation into the desired host of *C. glutamicum*. The incorporation of the mutation in the target gene or in the target sequence is achieved after homologous recombination by means of a first crossover event effecting integration and a second crossover event effecting an excision, and a recombinant bacterium is obtained.

Also it may be advantageous for the production of L-amino acids, in addition to the use of the aceA alleles according to the invention, at the same time also to enhance, in particular over-express, one or more enzymes of the respective biosynthesis pathway, glycolysis, anaplerosis, the citric acid cycle, the pentose phosphate cycle, amino acid export and possibly regulatory proteins. The use of endogenous genes is generally preferred.

The term "enhancement" describes in this connection the raising of the intracellular activity or concentration of one or more enzymes or proteins in a microorganism that are coded by the corresponding DNA, by for example increasing the number of copies of the gene or allele, or genes or alleles, by using a strong promoter or using a gene or allele that codes for a corresponding enzyme or protein having a high activity, and optionally by combining these measures.

By these enhancement measures, in particular over-expression, the activity or concentration of the corresponding protein is generally increased by at least 10%, 25%, 50%, 75%, 100%, 150%, 200%, 300%, 400% or 500%, at most up to 1000% or 2000%, referred to that of the wild type protein or to the activity or concentration of the protein in the starting microorganism.

Thus, for the production of L-lysine, in addition to the use of the alleles of the aceA gene according to the invention, at the same time one or more of the genes selected from the following group may be enhanced, in particular over-expressed:

the dapA gene coding for dihydrodipicolinate synthase (EP-B 0 197 335), the gap gene coding for glyceraldehyde-3-phosphate dehydrogenase (Eikmanns (1992), Journal of Bacteriology 174:6076–6086), the eno gene coding for enolase (DE: 19947791.4), the tpi gene coding for triose phosphate isomerase (Eikmanns (1992), Journal of Bacteriology 174:6076–6086), the pgk gene coding for 3-phosphoglycerate kinase (Eikmanns (1992), Journal of Bacteriology 174:6076–6086), the zwf gene coding for glucose-6-phosphate dehydrogenase (JP-A-09224661, EP-A-1108790), the pyc gene coding for pyruvate carboxylase (DE-A-198 31 609, EP-A-1108790), the mqo gene coding for malate-quinone oxidoreductase (Molenaar et al., European Journal of Biochemistry 254, 395–403 (1998)), the lysc gene coding for a feedback-resistant aspartate kinase (Accession No. P26512; EP-B-0387527; EP-A-0699759; WO 00/63388), the lysE gene coding for the lysine export protein (DE-A-195 48 222), the zwa1 gene coding for the Zwa1 protein (DE: 19959328.0, DSM 13115)

the gnd gene coding for 6-phosphogluconate dehydrogenase (WO 01/71012), the opcA gene coding for a subunit of glucose-6-phosphate dehydrogenase (Sequence No. 79 from WO 01/00844; WO 01/04322).

The enhancement of 6-phosphogluconate dehydrogenase may be achieved inter alia also by amino acid replacements, such as for example by replacing L-proline by L-serine, L-leucine, L-isoleucine or L-threonine at Position 158 of the enzyme protein and/or by replacing L-serine by L-phenylalanine or L-tyrosine at Position 361 of the enzyme protein.

The enhancement of the subunit of glucose-6-phosphate dehydrogenase for which the opcA gene codes may be achieved inter alia also by amino acid replacements, such as for example by replacing L-serine by L-phenylalanine or L-tyrosine at Position 312 of the enzyme protein.

Moreover, it may be advantageous for the production of L-lysine, in addition to the use of the alleles of the aceA gene according to the invention, at the same time to attenuate, in particular to reduce the expression, of one or more of the endogenous genes selected from the group:

the pck gene coding for phosphoenol pyruvate carboxykinase (DE 199 50 409.1, DSM 13047), the pgi gene coding for glucose-6-phosphate isomerase (U.S. Ser. No. 09/396,478, DSM 12969), the poxB gene coding for pyruvate oxidase (DE: 1995 1975.7, DSM 13114), the Zwa2 gene coding for the Zwa2 protein (DE: 19959327.2, DSM 13113), the fda gene coding for fructose-1,6-bisphosphate aldolase (Accession No. X17313; von der Osten et al., Molecular Microbiology 3 (11), 1625–1637 (1989)), the hom gene coding for homoserine dehydrogenase (EP-A-0131171), the thrB gene coding for homoserine kinase (Peoples, O. W., et al., Molecular Microbiology 2 (1988): 63–72) and the pfkB gene coding for phosphofructokinase (Sequence No. 57 from WO 01/00844).

The term "attenuation" describes in this connection the reduction or switching off of the intracellular activity of one or more enzymes (proteins) in a microorganism that are coded by the corresponding DNA, by using for example a weak promoter, or using a gene or allele that codes for a corresponding enzyme with a low activity, or inactivating the corresponding gene or enzyme (protein), and optionally combining these measures.

By means of these attenuation measures the activity or concentration of the corresponding protein is generally reduced to 0 to 75%, 0 to 50%, 0 to 25%, 0 to 10% or 0 to 5% of the activity or concentration of the wild type protein, or the activity or concentration of the protein in the starting microorganism.

The attenuation of the phosphofructokinase may also be achieved inter alia by amino acid replacements, such as for example by replacing L-leucine by L-alanine, L-glycine or L-proline at Position 109 of the enzyme protein.

The microorganisms produced according to the invention are also covered by the invention and may be cultivated continuously or batchwise in the batch process (batch cultivation) or in the fed batch process (feed process) or in the repeated fed batch process (repetitive feed process) for the purposes of producing L-amino acids. A summary of known cultivation methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Brunswick, Wiesbaden, 1994)).

The culture medium to be used must appropriately satisfy the requirements of the respective strains. Descriptions of culture media of various microorganisms are contained in the handbook "Manual of Methods for General Bacteriology" of the American Society for Bacteriology (Washington D.C., USA, 1981).

As carbon source, sugars and carbohydrates such as for example glucose, sucrose, lactose, fructose, maltose, molasses, starch and cellulose, oils and fats such as for example soya bean oil, sunflower oil, groundnut oil and coconut oil, fatty acids such as for example palmitic acid, stearic acid and linoleic acid, alcohols such as for example glycerol and ethanol, and organic acids such as for example acetic acid, may be used. These substances may be used individually or as a mixture.

As nitrogen source, organic nitrogen-containing compounds such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate may be used. The nitrogen sources may be used individually or as a mixture.

As phosphorus source, phosphoric acid, potassium dihydrogen phosphate or dipotassium hydrogen phosphate or the corresponding sodium-containing salts may be used. The culture medium must furthermore contain salts of metals, such as for example magnesium sulfate or iron sulfate, that are necessary for growth. Finally, essential growth promoters such as amino acids and vitamins may be used in addition to the aforementioned substances. Suitable precursors may furthermore be added to the culture medium. The afore-mentioned starting substances may be added to the culture in the form of a single batch or may be metered in in an appropriate manner during the cultivation.

In order to regulate the pH of the culture basic compounds such as sodium hydroxide, potassium hydroxide, ammonia or ammonia water, or acidic compounds such as phosphoric acid or sulfuric acid are used as appropriate. In order to control foam formation antifoaming agents such as for example fatty acid polyglycol esters may be used. In order to maintain the stability of plasmids, suitable selectively acting substances, for example antibiotics, may be added to the medium. In order to maintain aerobic conditions, oxygen or oxygen-containing gas mixtures such as for example air are fed into the culture. The temperature of the culture is normally 20° C. to 45° C., and preferably 25° C. to 40° C. Cultivation is continued until a maximum amount of the desired product has been formed. This target is normally achieved within 10 hours to 160 hours.

The following microorganism was deposited as a pure culture on 07.02.2003 at the Deutsche Sammlung für Mikroorganismen und Zellkulturen (DSMZ=German Collection of Microorganisms and Cell Cultures, Braunschweig, Germany) in accordance with the Budapest Treaty:

*Corynebacterium glutamicum* DSM5715_aceA_A332T as DSM 15431.

Methods for determining L-amino acids are known from the prior art. The analysis may be carried out for example by anion exchange chromatography followed by ninhydrin derivation, as described by Spackman et al. (Analytical Chemistry, 30, (1958), 1190), or by reversed phase HPLC, as described by Lindroth et al. (Analytical Chemistry (1979) 51: 1167–1174).

The process according to the invention can be used for the fermentative production of L-lysine.

The concentration of L-lysine may optionally be adjusted to the desired value by the addition of L-lysine.

EXAMPLE 1

Isolation and Sequencing of the DNA of the aceA Allele from the Strain DM1547.

The *Corynebacterium glutamicum* strain DM1547 was prepared from *C. glutamicum* ATCC13032 by multiple non-directed mutagenesis, selection and mutant choice. The strain is resistant to the lysine analogue S-(2-aminoethyl)-L-cysteine and methionine-sensitive.

Chromosomal DNA is isolated from the strain DM1547 by the conventional methods (Eikmanns et al., Microbiology 140, 1817–1828 (1994)). The polymerase chain reaction is used to amplify a DNA segment carrying the aceA gene or allele. The following oligonucleotide primers are chosen for the PCR on the basis of the sequence of the aceA gene which is known for *C. glutamicum* (Sequence No. 591 from Patent application WO 01/00844; Sequence No. 3489 and 7067 from Patent application No. EP-A_1108790; Genebank Accession Number X75504):

aceA–A1 (SEQ ID No. 8):

5' tac atc cgt act agc aac tc 3' aceA–A2 (SEQ ID No. 9):

5' atc cgt tgt aca gat gta gg 3'

The primers shown are synthesized by MWG Biotech (Ebersberg, Germany) and the PCR is carried out by the standard method of Innis et al. (PCR protocols. A Guide to Methods and Applications, 1990, Academic Press). The primers enable the amplification of an approximately 1.6 kb DNA segment carrying the aceA allele.

The amplified DNA fragment of approximately 1.6 kb, carrying the aceA allele of the strain DM1547, is identified by electrophoresis in 0.8% agarose gel, isolated from the gel and purified by the conventional methods (QIAquick Gel Extraction Kit, Qiagen, Hilden).

The nucleotide sequence of the amplified DNA fragment or PCR product is determined by GATC Biotech AG (Konstanz, Germany) by sequencing. The sequence of the PCR product is shown in SEQ ID No. 5. The sequence of the coding region is reproduced in SEQ ID No. 3. The amino acid sequence of the corresponding isocitrate lyase protein, found with the help of the Patentin program, is shown in SEQ ID No. 6 and SEQ ID No. 4.

Located in position 994 of the nucleotide sequence of the coding region of the aceA allele from the strain DM1547, i.e. in position 1251 of the nucleotide sequence shown in SEQ ID No. 5, is the base adenine. Located in the corresponding position of the wild-type gene is the base guanine (SEQ ID No. 1).

Located in position 332 of the amino acid sequence of the isocitrate lyase from the strain DM1547 is the amino acid threonine (SEQ ID No. 6 and SEQ ID No. 4). Located in the corresponding position of the wild-type protein is the amino acid alanine (SEQ ID No. 2).

The aceA allele, which contains the base adenine in position 994 of the coding region and accordingly codes for an isocitrate lyase containing the amino acid threonine in position 332 of the amino acid sequence, is called the aceA_A332T allele hereafter. In the name "aceA_A332T", A represents L-alanine, T represents L-threonine and 332 indicates the position of the amino acid replacement (cf. SEQ ID No. 2 and 4).

EXAMPLE 2

Replacement of the aceA Wild-Type Gene from the Strain DSM5715 with the aceA_A332T Allele 2.1 Preparation of a DNA Fragment Containing the Region of the aceA_A332T Allele in which the A332T Mutation is Located Chromosomal DNA is isolated from the strain DM1547 by the conventional methods (Eikmanns et al., Microbiology 140, 1817–1828 (1994)). The polymerase chain reaction is used to amplify a DNA segment carrying the part of the aceA allele which contains the mutation A332T. The following oligonucleotide primers are chosen for the PCR on the basis of the sequence of the aceA gene which is known for *C. glutamicum* (Sequence No. 591 from Patent application WO 01/00844; Sequence No. 3489 and 7067 from Patent application No. EP-A_1108790; Genebank Accession Number X75504):

aceA_XL-A1 (SEQ ID No. 10):

5' ga tct aga ttg gcg cac tca ccg gta ac 3' aceA_XL-A2 (SEQ ID No. 11):

5' ga tct aga cgc tac gga atc gca gat cg 3'

The primers shown are synthesized by MWG Biotech (Ebersberg, Germany) and the PCR is carried out by the standard method of Innis et al. (PCR protocols. A Guide to Methods and Applications, 1990, Academic Press). The primers enable the amplification of an approximately 1.6 kb DNA segment carrying a region of the aceA_A332T—allele which contains the A332T mutation (SEQ ID No. 7). The primers also contain the sequences for cleavage sites of the restriction endonuclease XbaI, which are underlined in the nucleotide sequence shown above.

The amplified DNA fragment of approximately 1.6 kb, carrying the aceA allele of the strain DM1547, is cleaved with the restriction endonuclease XbaI, identified by electrophoresis in 0.8% agarose gel, isolated from the gel and purified by the conventional methods (QIAquick Gel Extraction Kit, Qiagen, Hilden).

2.2 Construction of the Replacement Vector pK18mobsacB_aceA_A332T

The approximately 1.6 kb DNA fragment described in Example 2.1, cleaved with the restriction endonuclease XbaI and containing the aceA_A332T allele, is incorporated into the chromosome of the *C. glutamicum* strain DSM5715 by means of replacement mutagenesis with the aid of the sacB system described in Schäfer et al. (Gene 14, 69–73 (1994)). This system makes it possible to prepare or select allele replacements that take place through homologous recombination.

The mobilizable cloning vector pK18mobsacB is digested with the restriction enzyme XbaI and the ends are dephosphorylated with alkaline phosphatase (Boehringer Mannheim, Germany). The vector prepared in this way is mixed with the approximately 1.6 kb aceA_A332T fragment digested with the restriction enzyme XbaI, and the mixture is treated with T4 DNA ligase (Amersham-Pharmacia, Freiburg, Germany).

The *E. coli* strain S17-1 (Simon et al., Bio/Technologie 1, 784–791, 1993) is then transformed with the ligation mixture (Hanahan, in: DNA Cloning. A Practical Approach. Vol. 1, ILR-Press, Cold Spring Harbor, N.Y., 1989). The plasmid-carrying cells are selected by plating the transformation mixture on LB agar (Sambrook et al., Molecular Cloning: A Laboratory Manual. 2nd edition. Cold Spring Harbor, N.Y., 1989) supplemented with 25 mg/l of kanamycin.

Plasmid DNA is isolated from a transformant with the aid of the QIAprep Spin Miniprep Kit from Qiagen and checked by restriction cleavage with the enzyme BglII followed by agarose gel electrophoresis. The plasmid is called pK18mobsacB_aceA_A332T and is shown in FIG. 1.

2.3 Alleles Replacement

The vector pK18mobsacB_aceA_A332T mentioned in Example 2.2 is transferred to the *C. glutamicum* strain DSM5715 (EP-B-0435 132) by conjugation using a protocol of Schäfer et al. (Journal of Microbiology 172, 1663–1666 (1990)). The vector cannot replicate independently in DSM5715 and is only retained in the cell when it is integrated in the chromosome as the result of a recombination event. Transconjugants, i.e. clones with integrated pK18mobsacB_aceA_A332T, are selected by plating the conjugation mixture on LB agar (Sambrook et al., Molecular Cloning: A Laboratory Manual. 2nd edition. Cold Spring Harbor, N.Y., 1989) supplemented with 15 mg/l of kanamycin and 50 mg/l of nalidixic acid. Kanamycin-resistant transconjugants are streaked on plates of LB agar supplemented with 25 mg/l of kanamycin, and incubated for 24 hours at 33° C. To select mutants in which excision of the plasmid has taken place as the result of a second recombination event, the clones are cultivated non-selectively in LB liquid medium for 30 hours and then streaked on LB agar supplemented with 10% of sucrose, and incubated for 24 hours.

Like the starting plasmid pK18mobsacB, plasmid pK18mobsacB_aceA_A332T contains not only the kanamycin resistance gene but also a copy of the sacB gene coding for the levan sucrase from *Bacillus subtilis*. Expression inducible by sucrose leads to the formation of levan sucrase, which catalyses the synthesis of the product levan, toxic to *C. glutamicum*. Therefore, the only clones that grow on LB agar supplemented with sucrose are those in which the integrated pK18mobsacB_aceA_A332T has excised as the result of a second recombination event. Depending on the location of the second recombination event in relation to the mutation site, allele replacement or incorporation of the mutation takes place in the excision or the original copy remains in the chromosome of the host.

20 clones with the phenotype "growth in the presence of sucrose" and "non-growth in the presence of kanamycin" are examined by sequencing a region containing the mutation A332T of the aceA-gene, starting from the sequencing primer GATC-10790. The synthesis of the primer GATC-10790 and the sequencing is progressed by GATC Biotech AG (Konstanz, Germany) to identify clones carrying the aceA_A332T allele.

GATC-10790 (SEQ ID No. 12):

5' ACCGCAGAAGGCTACTACCA 3'

A clone containing the base adenine in position 994 of the coding region, and hence possessing the aceA_A332T allele, was identified in this way.

The strain was called *C. glutamicum* DSM5715_aceA_A332T.

EXAMPLE 3

Preparation of Lysine

The *C. glutamicum* strain DSM5715_aceA_A332T obtained in Example 2 is cultivated in a nutrient medium suitable for the production of lysine, and the lysine content is determined in the culture supernatant.

To do this, the strain is first incubated on an agar plate for 24 hours at 33° C. This agar plate culture is used to inoculate a preculture (10 ml of medium in a 100 ml conical flask). MM medium is used as the medium for the preculture.

The preculture is incubated on a shaker at 240 rpm for 24 hours at 33° C. This preculture is used to inoculate a main culture so that the initial OD (660 nm) of the main culture is 0.1. MM medium is also used for the main culture.

| MM medium | |
|---|---|
| CSL | 5 g/l |
| MOPS | 20 g/l |
| Glucose (separately autoclaved) | 50 g/l |
| Salts: | |
| $(NH_4)_2SO_4$ | 25 g/l |
| $KH_2PO_4$ | 0.1 g/l |
| $MgSO_4.7H_2O$ | 1.0 g/l |
| $CaCl_2.2H_2O$ | 10 mg/l |
| $FeSO_4.7H_2O$ | 10 mg/l |
| $MnSO_4.H_2O$ | 5.0 mg/l |
| Biotin (sterile-filtered) | 0.3 mg/l |
| Thiamine.HCl (sterile-filtered) | 0.2 mg/l |
| L-homoserine (sterile-filtered) | 0.4 g/l |
| $CaCO_3$ | 25 g/l |

The CSL (corn steep liquor), the MOPS (morpholinopropanesulfonic acid) and the salt solution are adjusted to pH 7 with aqueous ammonia and autoclaved. The sterile substrate and vitamin solutions and the dry-autoclaved $CaCO_3$ are then added.

Cultivation is carried out on a volume of 10 ml in a 100 ml conical flask with baffles at 33° C. and 80% atmospheric humidity.

After 48 hours the OD at a measurement wavelength of 660 nm is determined with a Biomek 1000 (Beckman Instruments GmbH, Munich). The amount of lysine formed is determined with an amino acid analyzer from Eppendorf-BioTronik (Hamburg, Germany) by means of ion exchange chromatography and post-column derivation with ninhydrin detection.

Table 1 shows the result of the experiment.

TABLE 1

| Strain | OD (660 nm) | Lysine-HCl g/l |
|---|---|---|
| DSM5715 | 8.2 | 15.3 |
| DSM5715_aceA_A332T | 7.4 | 16.2 |

BRIEF DESCRIPTION OF THE FIGURE

FIG. 1: Map of plasmid pK18mobsacB_aceA_A332T

The abbreviations and symbols used have the meanings given below. The numbers of base pairs indicated are approximate values obtained within the limits of reproducibility of the measurements.

| | |
|---|---|
| KanR: | kanamycin resistance gene |
| 'aceA: | cloned DNA fragment containing a 3'-terminal region of the aceA_A332T allele and the downstream region |
| sacB: | sacB gene |
| RP4mob: | mob region with the origin of replication for the transfer (oriT) |
| oriV: | origin of replication V |
| BglII: | cleavage site of the restriction enzyme BglII |
| XbaI: | cleavage site of the restriction enzyme XbaI |

What is claimed is:

1. A process for the production of L-lysine or feedstuffs additives containing L-lysine, comprising:
   a) fermenting coryneform bacteria in which alleles of the endogenous aceA gene are over-expressed under conditions that are suitable for the formation of the aceA gene product isocitrate lyase, and wherein said isocitrate lyase comprises the amino acid sequence of SEQ ID NO:2 in which the alanine residue at position 332 is replaced with threonine; and
   b) isolating said L-lysine or the feedstuffs additive containing L-lysine from the fermentation broth, optionally
   c) with constituents from the fermentation broth and/or biomass (>0 up to 100%).

2. The process of claim 1, wherein said L-lysine or said feedstuffs additive containing L-lysine is isolated with constituents from the fermentation broth and/or biomass (>0 up to 100%).

3. The process of claim 1, wherein coryneform bacteria are used in which, in addition to the over-expression of said aceA gene, further genes of the biosynthesis pathway of L-lysine are over-expressed.

4. The process of claim 1, wherein coryneform bacteria are used in which the metabolic pathways that reduce the formation of L-lysine are at least partially switched off.

5. A process for the production of L-lysine or feedstuffs additives containing L-lysine, comprising:
   a) fermenting coryneform bacteria that contain endogenous nucleotide sequences coding for the enzyme isocitrate lyase, wherein in the associated amino acid sequences the L-alanine at position 332 is replaced by L-threonine,
   b) optionally enriching the L-lysine in the fermentation broth,
   c) isolating the L-lysine or the feedstuffs additive containing L-lysine from the fermentation broth, optionally
   d) with constituents from the fermentation broth and/or from the biomass (>0 up to 100%).

6. The process of claim 5, wherein the endogenous nucleotide sequences coding for the enzyme isocitrate lyase are over-expressed under conditions that are suitable for the formation of the aceA gene product isocitrate lyase.

7. The process of either claim 1 or 5, wherein the *Corynebacterium glutamicum* strain DSM5715_aceA_A332T is employed.

8. The process of any one of claims 1–6, wherein said isocitrate lyase is encoded by DNA with the nucleotide sequence of SEQ ID NO:3.

9. The process of any one of claims 1–6, wherein said isocitrate lyase consists of the amino acid sequence of SEQ ID NO:2 in which the alanine residue at position 332 is replaced with threomne.

10. The process of either claim 1 or 5, wherein the activity of said isocitrate lyase is increased by at least 50%.

* * * * *